US00PP37539P2

(12) United States Plant Patent
Roper

(10) Patent No.: US PP37,539 P2
(45) Date of Patent: Jul. 28, 2026

(54) ALMOND TREE NAMED 'Franklin'

(50) Latin Name: *Prunus dulcis*
Varietal Denomination: 'Franklin'

(71) Applicant: Utah State University, Logan, UT (US)

(72) Inventor: Teryl Roper, Newton, MA (US)

(73) Assignee: Utah State University, Logan, UT (US)

( * ) Notice: Subject to any disclaimer, the term of this patent is extended or adjusted under 35 U.S.C. 154(b) by 0 days.

(21) Appl. No.: 19/055,996

(22) Filed: Feb. 18, 2025

(51) Int. Cl.
*A01H 5/08* (2018.01)
*A01H 5/00* (2018.01)
*A01H 6/74* (2018.01)

(52) U.S. Cl.
USPC ..... Plt./155
CPC ..... *A01H 6/7427* (2018.05); *A01H 5/00* (2013.01)

(58) Field of Classification Search
USPC ..... Plt./152, 155
See application file for complete search history.

(56) References Cited

U.S. PATENT DOCUMENTS

PP35,678 P2 * 3/2024 Slaughter ..... A01H 6/7427 Plt./155

* cited by examiner

*Primary Examiner* — Karen M Redden
(74) *Attorney, Agent, or Firm* — G. Harley Blosser; Sandberg Phoenix & von Gontard, PC

(57) ABSTRACT

A new and distinct cultivar of almond tree (*Prunus dulcis*) designated as 'Franklin' originated from seed collected in Bostanlik, Uzbekistan, and was developed through evaluation at Utah State University. The cultivar is characterized by uniform oval nuts averaging 2.7 grams in shell with one-gram sweet kernels, with high-quality shell integrity, pale pink to white flowers, late September maturity, and successful asexual propagation through grafting and budding onto both peach and almond rootstocks.

5 Drawing Sheets

Current name or designation: The 'Franklin' almond tree (*Prunus dulcis*)

General statements: The information below relates to a new and distinct variety/cultivar of almond tree (*Prunus dulcis*).

DEVELOPMENT

The 'Franklin' almond tree (*Prunus dulcis*), was developed through international germplasm collection efforts and is of unknown (not patented) parentage. The cultivar's genetic material originates from a seed, based on best information which is believed to have been collected in a cultivated area in an unknown area of the Bostanlik region of Uzbekistan. Following acquisition through official plant import permits, the genetic material was propagated in greenhouse facilities located in Richmond, Utah. The cultivar's development continued through field trials conducted in Thatcher, Box Elder County, Utah, where the initial evaluation orchard remains established.

PROPAGATION

Asexual reproduction of this new and distinct variety of almond tree has been accomplished through grafting and budding techniques onto both peach and almond rootstocks. Initial propagation trials were conducted at the Utah State University research facilities in Richmond, Utah. The compatibility with multiple understocks provides flexibility in cultivation, allowing growers to select appropriate rootstock based on local soil conditions and climate factors. Subsequent evaluations of these asexually reproduced specimens have demonstrated that the asexual reproductions maintain fidelity to the original tree. All characteristics of the original specimen appear to be transmitted through succeeding asexual propagations, ensuring consistent trait expression across propagated specimens.

UNIQUENESS

The 'Franklin' almond tree (*Prunus dulcis*) exhibits morphological and agronomic characteristics that, in combination, distinguish it from existing cultivars. As its parentage is unknown, the 'Franklin' Almond Tree is compared herein to a related type/variety of almond tree, named the 'Bennett-Hickman' (U.S. Plant Pat. No. 26,083P3), also of unknown parentage. Compared to the 'Bennett-Hickman' and other almond trees, the 'Franklin' almond tree produces immature fruit before the husk dehisces which is ovoid, and the shape of the almond nut in the shell is uniformly formed as asymmetrically oval nuts as shown in the accompanying drawings (photos) with an average in-shell weight of 2.7 grams, containing kernels that consistently measure approximately one gram. The floral display consists of pale pink to white petals, typical of the species but contributing to the tree's ornamental value. The 'Franklin' almond tree uniformly maintains high quality shell integrity, which makes reference to the shells remaining intact with both halves of the shells remaining connected to protect the kernel through harvest. The hard shell characteristic provides protection for the sweet-flavored kernel within, while maintaining consistent kernel-to-shell ratios across harvests. This combination of nut size, shell hardness, and kernel quality creates a unique cultivar profile within the existing almond germplasm.

PRODUCTION AND HARVESTING

The 'Franklin' almond tree requires standard orchard cultivation practices, with emphasis on full sun exposure and well-drained soil conditions. Flowering phenology aligns with or slightly precedes that of peach blossoms, positioning harvest operations in late September. The cultivar exhibits obligate cross-pollination requirements, being non-self-fruitful and necessitating appropriate pollinizer cultivars for commercial production. Site selection should prioritize areas with adequate soil drainage and exposure to facilitate optimal tree health and nut development. Cultural practices typical of commercial almond production are suitable for this cultivar, with timing of operations determined by its specific bloom-to-harvest interval.

PHOTOGRAPHS ACCOMPANYING SUBMISSION

The photographs submitted herewith show the color of our new variety/cultivar as nearly as reasonably possible to make the same in a color illustration of this character (with reference to The Royal Horticultural Society, (London) Colour Chart, aka the "RHSCC" herein:

DESCRIPTION OF THE NEW CULTIVAR

Figure 1:
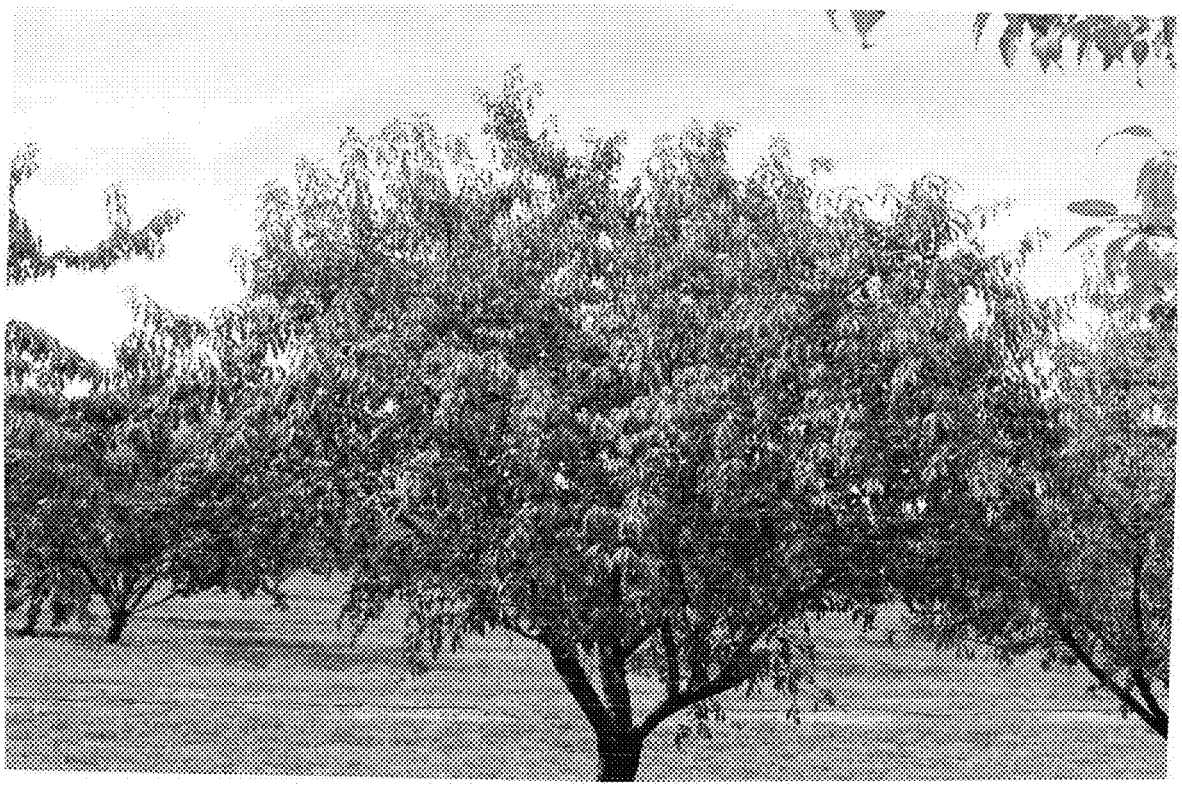
FIG. 1 is a photograph of an estimated 10-year old specimen of the new and distinct variety 'Franklin almond tree'.
Figure 2:
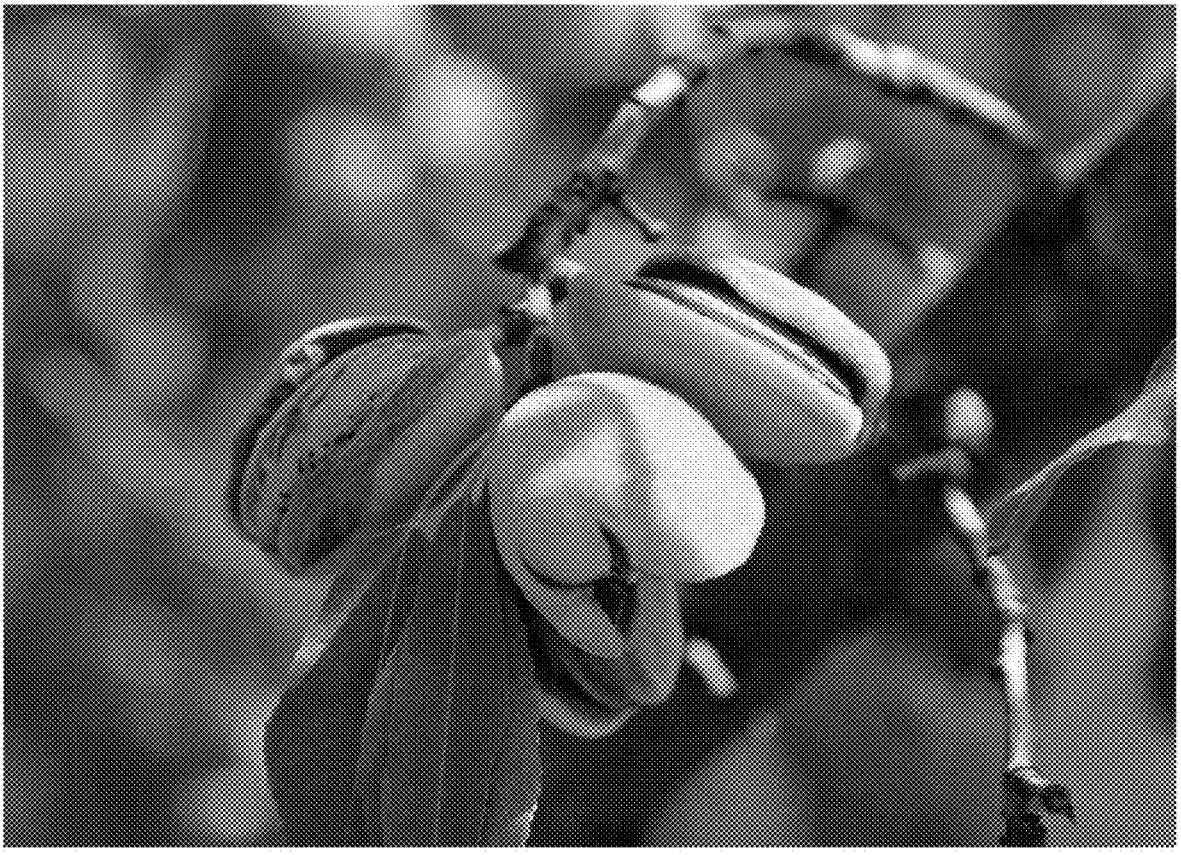
FIG. 2 is a photograph of the closed blossoms of the tree of FIG. 1.
Figure 3:
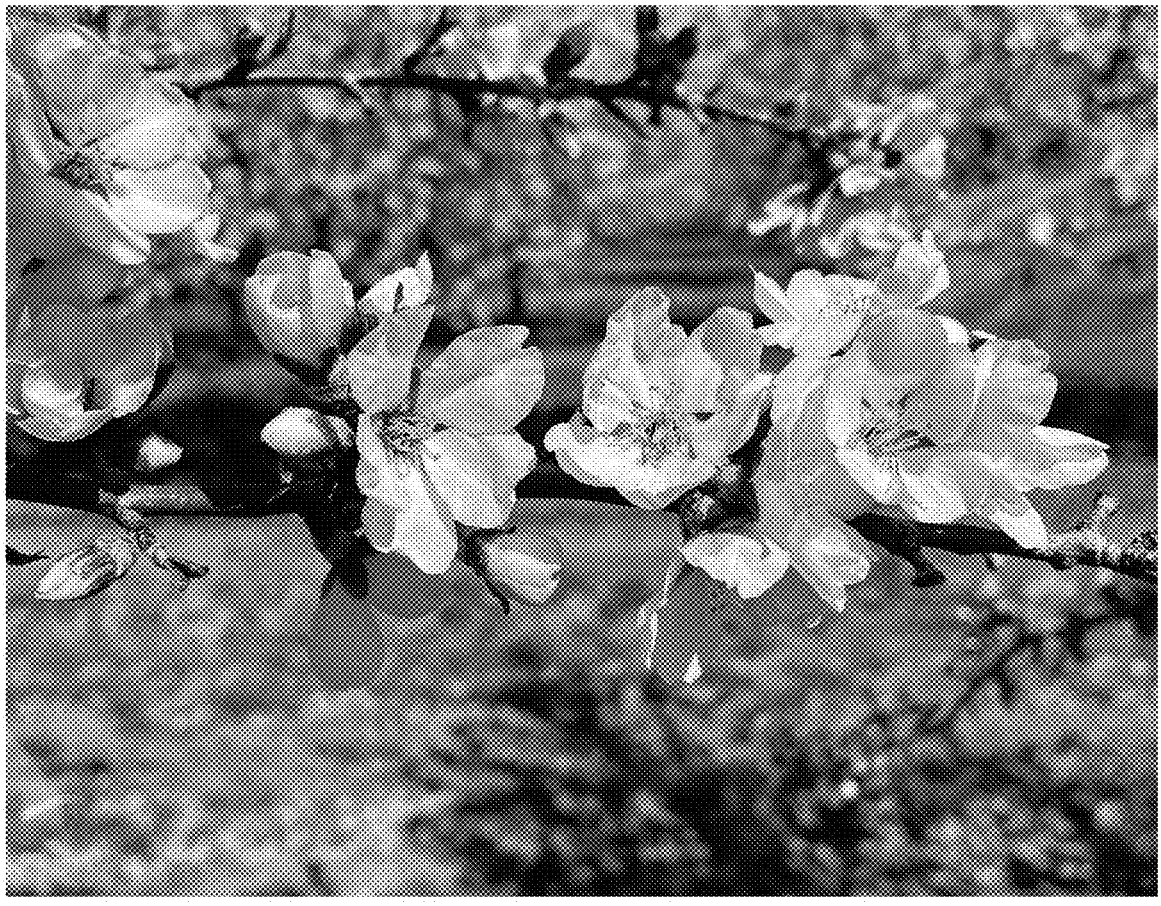
FIG. 3 is a photograph of the open blossoms of the tree of FIG. 1.
Figure 4:
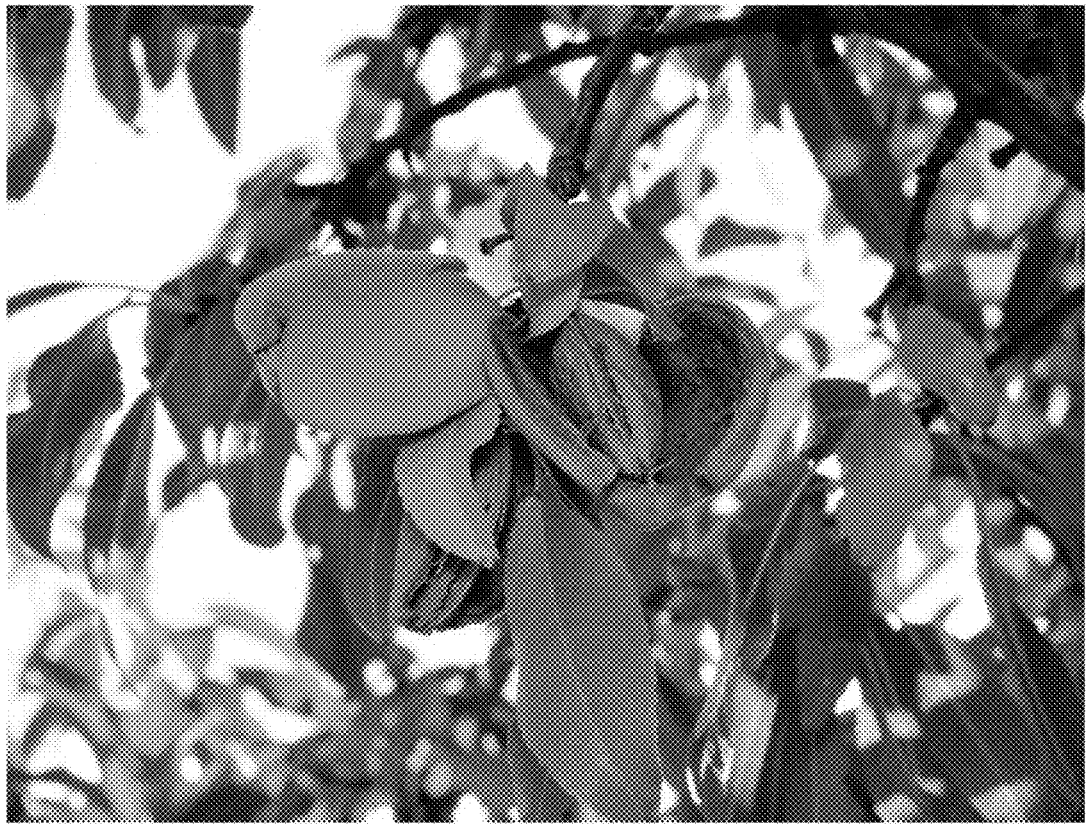
FIG. 4 is a photograph of the limb and blossom habit of the tree of FIG. 1.
Figure 5:
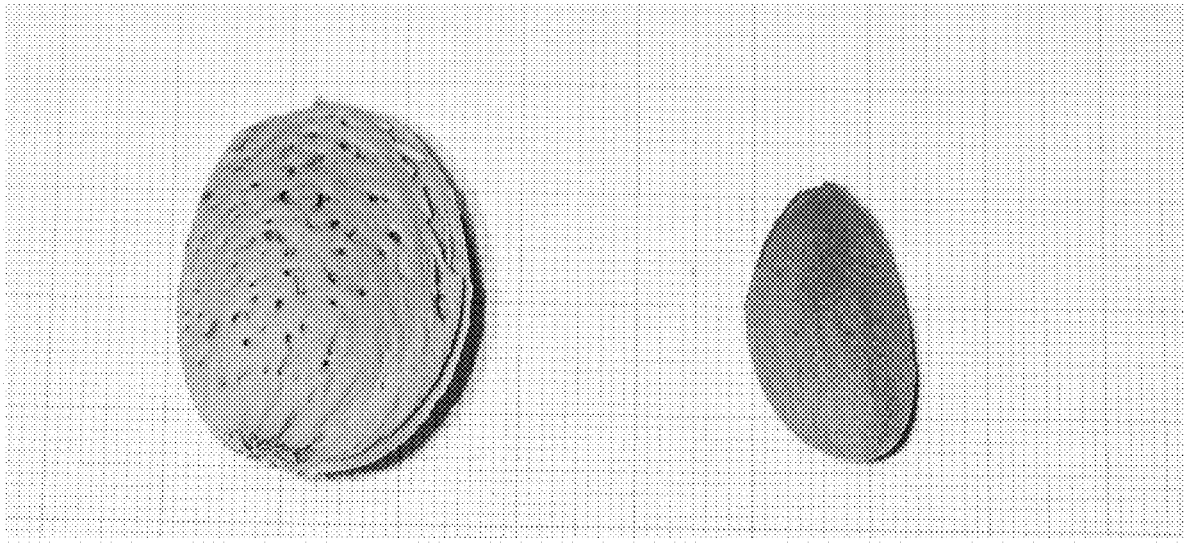
FIG. 5 is a photograph of the almond of the tree of FIG. 1.

The following is a detailed description of our new cultivar of almond tree 'Franklin' Other than as set forth above and below, as of this time, no other characteristics of our new almond tree 'Franklin' have been observed by the inventors which appear to be substantially different from the characteristics common to almond trees.

Classification:

*Family*.—Rosaceae.

*Botanical*.—*Prunus dulcis*.

*Common*.—Almond.

*Denomination*.—'Franklin'.

General description:

*Plant type*.—Nut tree.

*Propagation type*.—Asexual via grafting or budding. Peach and almond are compatible understocks.

*Height from soil level to top of foliage*.—5-6 meters, allowing for rootstock effect.

*Plant spread*.—4 meters, depending on adjacent plants & pruning.

*Number of basal shoots per plant*.—One.

*Growth rate*.—Typically ranges from 8 to 10 inches, especially as a young tree.

*Propagation type*.—Asexual via budding or grafting.

*Time to initiate rooting*.—Does not root from cuttings.

*Time to develop roots*.—Does not root from cuttings.

Stem/trunk:

*Length*.—1 meter or more depending on pruning method.

*Diameter*.—30 cm.

*Shape*.—Rounding canopy.

*Color*.—Trunk is yellowish brown (RHSCC N167A).

*Texture*.—Smooth, becoming corky with age.

*Strength*.—Typical for almond.

*Lenticels*.—Present.

*Lenticel color*.—Silvery gray.

Branches:

*Length*.—1-2 m.

*Diameter*.—Variable.

*Color*.—Branches are yellowish brown (RHSCC 175D).

Foliage description:

*Approximate no. of leaves per plant*.—Thousands to tens of thousands.

*Arrangement*.—Spiral.

*Length*.—8-13 cm.

*Width*.—3 cm at midpoint.

*Shape, general*.—Linear.

*Shape of apex*.—Acute.

*Shape of base*.—Acute.

*Margin*.—Slightly serrulate.

*Upper surface texture*.—Smooth.

*Lower surface texture*.—Smooth.

*Color* (*defined for young foliage, mature foliage, fall foliage*).—Young and mature foliage is dusty green (RHSCC 197-B). Fall foliage is yellow (RHSCC 15-A).

*Cataphyll*.—None.

*Inflorescence*.—Monopetal. Flowers and fruit are borne on long spurs. Petals are light pink and are typical for *Prunus* species. Not self-pollinating. Flowering is with or slightly earlier than fellow *Prunus* peach trees grown adjacent.

*Cold tolerance*.—Hardy to USDA Hardiness zone 6b.

*Disease and pest tolerance*.—The 'Franklin' almond is susceptible to common pests and diseases typical for almond trees, some of which include crown gall (*Agrobacterium tumefaciens*), white prunicola scale (*Pseudaulacaspis prunicola*), the Fruit-tree leafroller (*Archips argyrospila*), blossom blight fungus (primarily *Monilinia fruticola*), tree mites (*Aculus fockeui*), and shothole funus ((*Wilsonomyces carpophilus*).

*Fruit and seed set*.—Hard shell almond with sweet kernels. Nuts are large with hard shells with a mean weight in 2021 of 2.7 grams in the shell. 2021 yield was 7.39 kg/tree with total kernel weight of 4.7 kg/tree. Nuts mature in late September to early October in Northern Utah. Shells are semi-hard with good shell integrity. Kernels are smooth, plump, and asymmetrically shaped.

*Drought tolerance*.—Typical for almond and depends in part on rootstock with 1 inch in range of every 10 days anticipated.

*Taste*.—Sweet kernels.

*Aroma*.—Not appreciably aromatic.

*Characteristics of the plant in winter dormancy*.—In northern Utah, leaf drop occurs in October. The tree is hardy to USDA hardiness zone 6b. Spring flowering is similar in timing to peaches.

The invention claimed is:

1. A new and distinct variety of almond tree named 'Franklin', as described and illustrated herein.

* * * * *